(12) United States Patent
Burkholz et al.

(10) Patent No.: US 11,617,864 B2
(45) Date of Patent: Apr. 4, 2023

(54) COMPLIANT CATHETER ADAPTER AND COMPRESSION CAP

(71) Applicant: Becton, Dickinson and Company, Franklin Lakes, NJ (US)

(72) Inventors: Jonathan Karl Burkholz, Salt Lake City, UT (US); Ralph L. Sonderegger, Farmington, UT (US); Bart D. Peterson, Farmington, UT (US); Bin Wang, Sandy, UT (US); Olivia Hu, Shanghai (CN); Neville Chia, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 519 days.

(21) Appl. No.: 16/774,230

(22) Filed: Jan. 28, 2020

(65) Prior Publication Data

US 2020/0155809 A1 May 21, 2020

Related U.S. Application Data

(62) Division of application No. 15/286,287, filed on Oct. 5, 2016, now Pat. No. 10,549,073.

(Continued)

(51) Int. Cl.
*A61M 25/06* (2006.01)
*A61M 5/158* (2006.01)
(Continued)

(52) U.S. Cl.
CPC ........ *A61M 25/0637* (2013.01); *A61M 5/158* (2013.01); *A61M 5/3202* (2013.01);
(Continued)

(58) Field of Classification Search
CPC ............ A61M 25/0637; A61M 5/3202; A61M 25/0606
(Continued)

(56) References Cited

U.S. PATENT DOCUMENTS 5,059,186 A * 10/1991 Yamamoto ......... A61M 25/0111
604/167.03
5,531,720 A 7/1996 Atkins
(Continued)

FOREIGN PATENT DOCUMENTS

CN 207168788 4/2018
EP 0732120 9/1996
(Continued)

*Primary Examiner* — Phillip A Gray
(74) *Attorney, Agent, or Firm* — Kirton McConkie; Whitney Blair; Kevin Stinger

(57) ABSTRACT

A compliant catheter adapter may include a catheter adapter body formed of a compliant material. The catheter adapter body may have a generally elongate shape and an inner chamber. The catheter adapter body may include a compression resistant septum disposed toward the proximal end of the catheter adapter body. The compression resistant septum may have a lumen configured to receive an elongate object. The compression resistant septum may also be coupled to a compression cap that imparts a compression force on the compression resistant septum such that the lumen narrows and seals when the elongate object is removed from the lumen.

20 Claims, 13 Drawing Sheets

Related U.S. Application Data

(60) Provisional application No. 62/296,383, filed on Feb. 17, 2016, provisional application No. 62/296,385, filed on Feb. 17, 2016, provisional application No. 62/247,599, filed on Oct. 28, 2015, provisional application No. 62/247,621, filed on Oct. 28, 2015, provisional application No. 62/247,617, filed on Oct. 28, 2015, provisional application No. 62/247,624, filed on Oct. 28, 2015, provisional application No. 62/247,596, filed on Oct. 28, 2015, provisional application No. 62/247,607, filed on Oct. 28, 2015, provisional application No. 62/247,626, filed on Oct. 28, 2015.

(51) Int. Cl.
*A61M 5/32* (2006.01)
*A61M 39/06* (2006.01)

(52) U.S. Cl.
CPC ..... *A61M 25/0606* (2013.01); *A61M 39/0613* (2013.01); *A61M 2039/062* (2013.01)

(58) Field of Classification Search
USPC .................................................. 604/167.02
See application file for complete search history.

(56) References Cited

U.S. PATENT DOCUMENTS

| | | |
|---|---|---|
| D458,678 S | 6/2002 | Cindrich |
| 2009/0254050 A1 | 10/2009 | Bottcher |

FOREIGN PATENT DOCUMENTS

| | | |
|---|---|---|
| EP | 2044970 | 4/2009 |
| GB | 2508466 | 6/2014 |
| JP | 2014510574 | 5/2014 |
| WO | 02/096495 | 12/2002 |
| WO | 2004/032995 | 4/2004 |
| WO | 2006/067660 | 6/2006 |
| WO | 2007/050788 | 5/2007 |

\* cited by examiner

COMPLIANT CATHETER ADAPTER AND COMPRESSION CAP

RELATED APPLICATIONS

This application is a divisional of U.S. Provisional patent application Ser. No. 15/286,287, which was filed Oct. 5, 2016, and is entitled COMPLIANT CATHETER ADAPTER AND COMPRESSION CAP, which claims the benefit of U.S. Provisional Patent Application Ser. No. 62/247,607, which was filed Oct. 28, 2015, U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application No. 62/247,617, which was filed on Oct. 28, 2015, U.S. Provisional Patent Application Ser. No. 62/247,621, which was filed Oct. 28, 2015, U.S. Provisional Patent Application Ser. No. 62/247,624, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

FIELD OF THE INVENTION

The present disclosure relates to catheters. More specifically, the present disclosure relates to compliant catheter adapters including compression caps to facilitate retention and compression of catheter adapter septa.

BACKGROUND OF THE INVENTION

Intravascular (IV) catheters may be used to infuse fluids into the vascular system of a patient, such as saline solution, various medicaments, total parenteral nutrition, etc. IV catheters may also be used to withdraw blood from the patient or to monitor various parameters of the patient's vascular system.

Peripheral IV catheters may be relatively short (typically on the order of about two inches or less in length). The most common type of IV catheter is an over-the-needle peripheral IV catheter. As its name implies, an over-the-needle IV catheter is mounted over an introducer needle having a sharp distal tip. At least the distal portion of the catheter tightly engages the outer surface of the needle to prevent "peelback" of the catheter and thus facilitates insertion of the catheter into the blood vessel. The distal tip of the introducer needle may extend beyond the distal tip of the catheter with the bevel of the needle facing up away from the patient's skin.

The catheter and introducer needle assembly may be inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

In order to verify proper placement of the catheter in the blood vessel, the clinician may confirm that there is flashback of blood in a flashback chamber. The flashback chamber is typically formed as part of a needle component or needle hub. Alternatively, the introducer needle could include a notch or opening formed along a distal portion thereof so that the blood flashback can be observed in the annular space between the introducer needle and the catheter when the catheter is transparent or at least translucent. The clinician may then withdraw the introducer needle, leaving the catheter in place, and/or attach an appropriate device to the catheter. Such a device can include a fluid delivery device, a PRN, a deadender cap, a blood pressure monitoring probe, etc.

One common method of administering fluids into a patient's blood flow is through an intravenous delivery system. Intravenous delivery systems may include a liquid source such as a liquid bag, a drip chamber used to determine the flow rate of fluid from the liquid bag, tubing for providing a connection between the liquid bag and the patient, and an intravenous access unit, such as a catheter, that is positioned intravenously in the patient. The catheter may include a catheter adapter with one or more connectors or ports that are configured to allow "piggybacking" of intravenous delivery systems which may be used to administer medicine, among other functions.

Although typical IV catheter and introducer needle assemblies generally perform their functions satisfactorily, they do have certain drawbacks. For example, the procedure for properly placing a catheter into a patient's blood vessel can result in a significant amount of blood leakage from the catheter between the initial venipuncture and the time that an appropriate device is connected to the catheter. This blood leakage is problematic because of potential contamination to a clinician from an infected patient. This is especially worrisome because of diseases such as Acquired Immune Deficiency Syndrome ("AIDS") which can be transmitted by the exchange of body fluids from an infected person to another person.

In order to minimize blood leakage, a self-sealing septum may be placed in the proximal end of the catheter adapter. The septum allows the introducer needle to extend through the septum and the catheter to allow the catheter to be placed into a patient's blood vessel. In addition, the septum allows the clinician to withdraw the introducer needle from the catheter and the septum, which then closes after the introducer needle has been completely withdrawn from the catheter hub. This arrangement may minimize blood leakage from the catheter adapter. The use of a septum may significantly increase the force that the clinician needs to exert on the introducer needle in order to withdraw the introducer needle from the catheter. Additionally, if the introducer needle is located in the septum for extended periods of time, the septum may take a compression set about the introducer needle preventing the septum from completely sealing once the introducer needle is withdrawn from the septum.

Once the catheter has been placed in a patients' vein, and the introducer needle has been removed, the clinician will typically secure the catheter adapter body to the patient's skin to prevent accidental removal of the catheter from the patient's vein. However, catheter adapter bodies are typically formed with rigid materials that do not conform well to the patient's skin and are not comfortable. Moreover, catheter adapter bodies formed of many different materials may be more expensive and difficult to manufacture because of their complexity. Accordingly, there is a need for soft body catheter adapters that better conform to the patient's body, improve patient comfort, and can be more securely affixed to the patient. Moreover, soft body catheter adapters may achieve a reduced cost of manufacture because they may be substantially molded from a single compliant material in an integral fashion, thus reducing the number and/or amount of different materials that may be needed during the manufacturing process.

SUMMARY OF THE INVENTION

In some embodiments, a compliant catheter adapter may include a catheter adapter body formed of a compliant material. For example, some embodiments of the present invention comprise a compliant material having a durometer hardness of from approximately 30 Shore A to approximately 90 Shore D. In some embodiments, a compliant material comprises a durometer hardness of from approximately 50 Shore A to approximately 90 Shore D. The catheter adapter body may have a proximal end, a distal end, and a generally elongate shape formed about a longitudinal axis extending between the proximal end and the distal end of the catheter adapter body. The catheter adapter body may also have an inner chamber with a generally elongate shape formed about the longitudinal axis. The catheter adapter body may further include a compression resistant septum that is formed in the compliant material of the catheter adapter body and disposed toward the proximal end of the catheter adapter body. The compression resistant septum may also have a lumen that is configured to receive an elongate object. The compression resistant septum may be further coupled to a compression cap that imparts a compression force on the compression resistant septum such that the lumen narrows and seals when the elongate object is removed from the lumen. In some instances, the compression force comprises radial and axial compression forces.

In other embodiments, a compliant catheter adapter may include a catheter adapter body formed of a compliant material. The catheter adapter body may have a proximal end, a distal end, and a generally elongate shape formed about a longitudinal axis extending between the proximal end and the distal end of the catheter adapter body. The catheter adapter body may also have an inner chamber with a generally elongate shape formed about the longitudinal axis. The catheter adapter body may further include a first compression resistant septum abutted against a second compression resistant septum. The first compression resistant septum may have a first lumen, and the second compression resistant septum may have a second lumen, both of which are configured to receive an elongate object. The first and second compression resistant septa may be further coupled to a compression cap that imparts a compression force on the first and second compression resistant septa such that the first and second lumens narrow and seal when the elongate object is removed from the first and second lumens. In some instances, the compression force comprises radial and axial compression forces.

In yet other embodiments, a catheter system may include a needle component having a needle hub, a needle coupled to the needle hub, and a grip coupled to the needle hub. The catheter system may also include a compliant catheter adapter having a catheter adapter body formed of a compliant material. The catheter adapter body may have a proximal end, a distal end, and a generally elongate shape formed about a longitudinal axis extending between the proximal end and the distal end of the catheter adapter body. The catheter adapter body may also have an inner chamber with a generally elongate shape formed about the longitudinal axis. The catheter adapter body may further include a compression resistant septum that is formed in the compliant material of the catheter adapter body and disposed toward the proximal end of the catheter adapter body. The compression resistant septum may also have a lumen that is configured to receive an elongate object. The compression resistant septum may be further coupled to a compression cap that imparts a compression force on the compression resistant septum such that the lumen narrows and seals when the elongate object is removed from the lumen. In some instances, the compression force comprises radial and axial compression forces.

These and other features and advantages of the present disclosure may be incorporated into certain embodiments and will become more fully apparent from the following description and appended claims, or may be learned by the practice of the present disclosure as set forth hereinafter. The present disclosure does not require that all the advantageous features and all the advantages described herein be incorporated into every embodiment.

BRIEF DESCRIPTION OF THE DRAWINGS

Exemplary embodiments of the present disclosure will become more fully apparent from the following description and appended claims, taken in conjunction with the accompanying drawings. Understanding that these drawings depict only exemplary embodiments and are therefore not to be considered limiting of the disclosure's scope, the exemplary embodiments of the present disclosure will be described with additional specificity and detail through use of the accompanying drawings in which:

DETAILED DESCRIPTION OF THE INVENTION

Figure 1A:
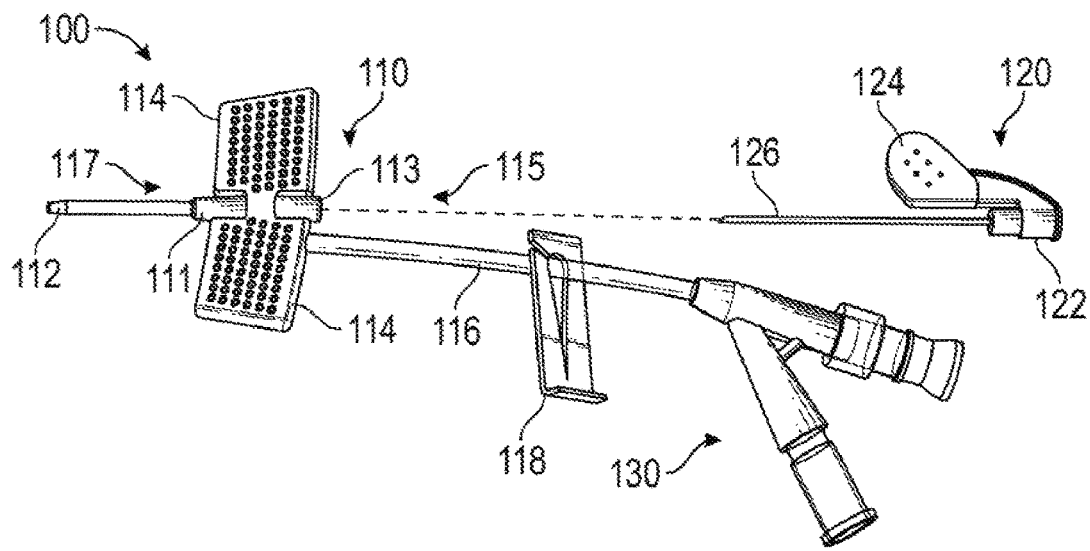
FIG. 1A is an isometric view of an IV catheter set showing a needle component removed from a catheter adapter, according to one embodiment of the present disclosure.

The presently preferred embodiments of the present disclosure may be understood by reference to the drawings, wherein like parts may be designated by like numerals throughout. It will be readily understood that the components of the present disclosure, as generally described and illustrated in the Figures, could be arranged and designed in a wide variety of different configurations. Thus, the following more detailed description is not intended to limit the scope of the present disclosure as claimed, but is merely representative of presently preferred embodiments.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1B:
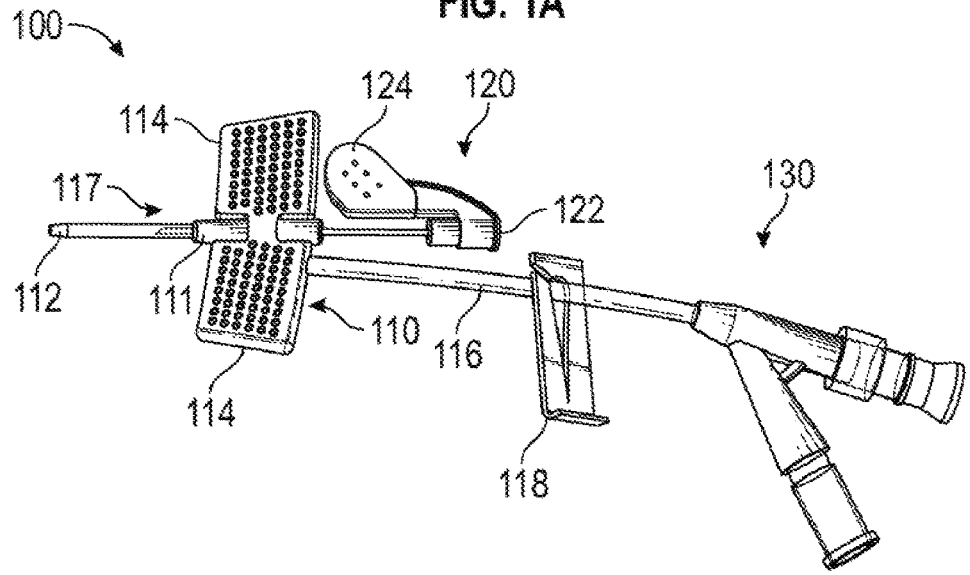
FIG. 1B is an isometric view of the IV catheter set of FIG. 1A with the needle component partially inserted into the catheter adapter.
Figure 1C:
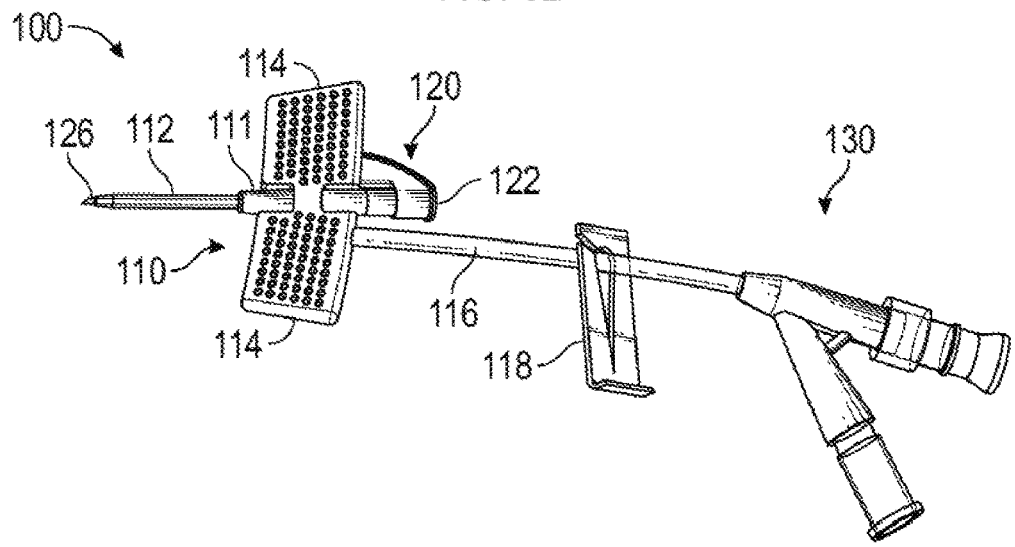
FIG. 1C is an isometric view of the IV catheter set of FIG. 1A with the needle component fully inserted into the catheter adapter.

FIGS. 1A-1C illustrate various isometric views of an IV catheter set 100, according to one embodiment of the present disclosure. The IV catheter set 100 may generally include a compliant catheter adapter 110, a needle component 120, an extension tube 116, a slide clamp 118, and an infusion set 130. FIG. 1A shows the IV catheter set 100 with the needle component 120 removed from the compliant catheter adapter 110. FIG. 1B shows the IV catheter set 100 with the needle component 120 partially inserted into the compliant catheter adapter 110 and FIG. 1C shows the IV catheter set 100 with the needle component 120 fully inserted into the compliant catheter adapter 110.

The compliant catheter adapter 110 may include a catheter adapter body 111 formed of a compliant material. A compliant material generally comprises a soft, flexible polymer material that may be comfortable against the skin of a patient. For example, some embodiments of the present invention comprise a compliant material having a durometer hardness of from approximately 30 Shore A to approximately 90 Shore D. In some embodiments, a compliant material comprises a durometer hardness of from approximately 50 Shore A to approximately 90 Shore D. The catheter adapter body 111 may be integrally formed from a compression set resistant elastomeric material including, but not limited to: a thermoplastic elastomer material, a liquid silicone rubber material, a polyisoprene material, and the like. In at least some embodiments, the catheter adapter body 111 may be substantially formed from a single compression set resistant elastomeric material. The compliant catheter adapter 110 may also include a compression cap 113, one or more stabilization members 114, and a catheter lumen 112, as will be discussed in more detail below.

The compliant catheter adapter 110 may include a feature that allows the compliant catheter adapter 110 to be coupled to an extension tube 116. The extension tube 116 may pass through a slide clamp 118 and couple to an infusion set 130. The infusion set 130 may include one or more connectors or injection ports that allow intravenous fluid communication with the patient, as generally known in the art.

The needle component 120 may include a needle hub 122, a grip 124 coupled to the needle hub 122, and an elongate object coupled to the needle hub 122 (such as a needle 126). The needle component 120 may be used to facilitate insertion of the catheter lumen 112 into a vein of a patient (not shown). The embodiment shown in FIG. 1A illustrates a grip 124 having a paddle-like shape or style. However, in other embodiments the grip 124 may include any number of suitable shapes and styles including but not limited to: paddle grips, straight grips, ported grips, etc. For example, FIGS. 2A-2C, 4A-5, and 6B-8 illustrate various examples of grips having different shapes and styles. Likewise, the needle hub 122 may also include any number of suitable shapes and styles.

Figure 2A:
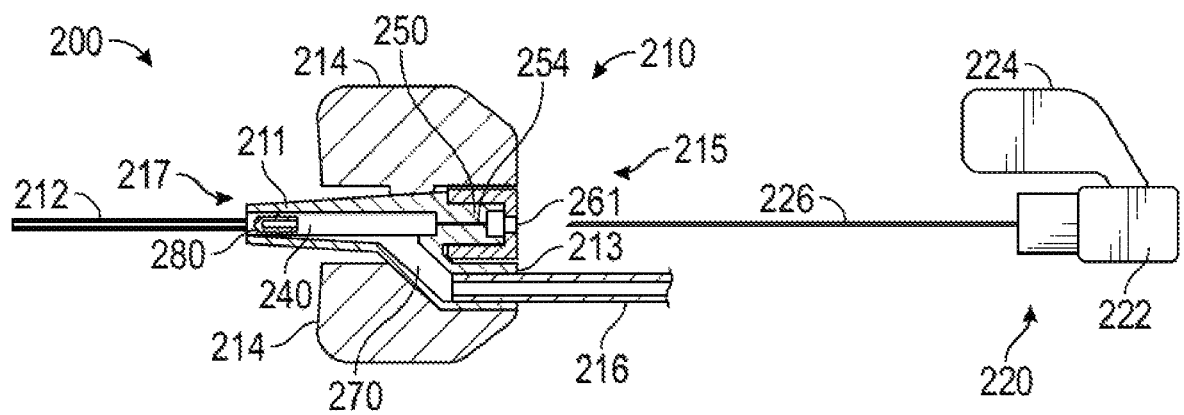
FIG. 2A is a cross-sectional side view of a catheter system with a needle component removed from a catheter adapter, according to another embodiment of the present disclosure.
Figure 2B:
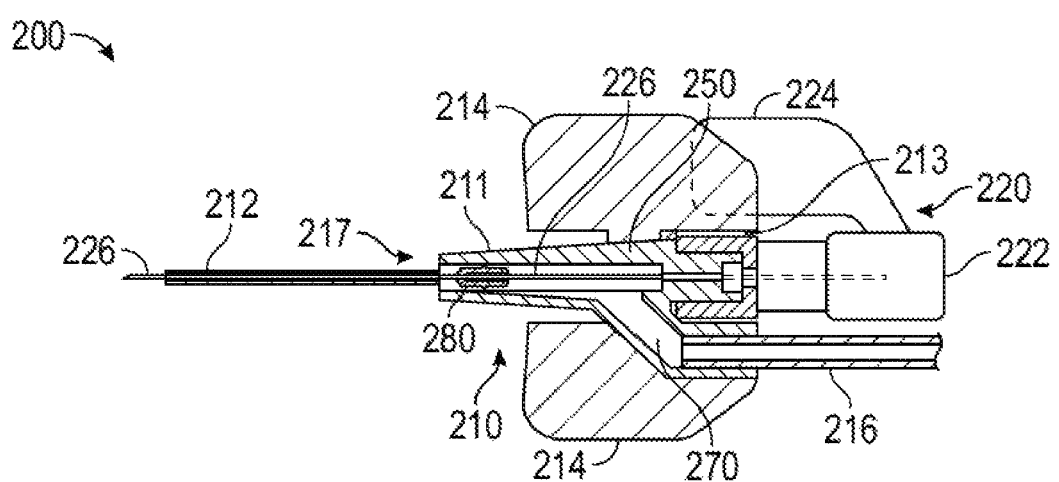
FIG. 2B is a cross-sectional side view of the catheter system of FIG. 2A with the needle component fully inserted into the catheter adapter.
Figure 2C:
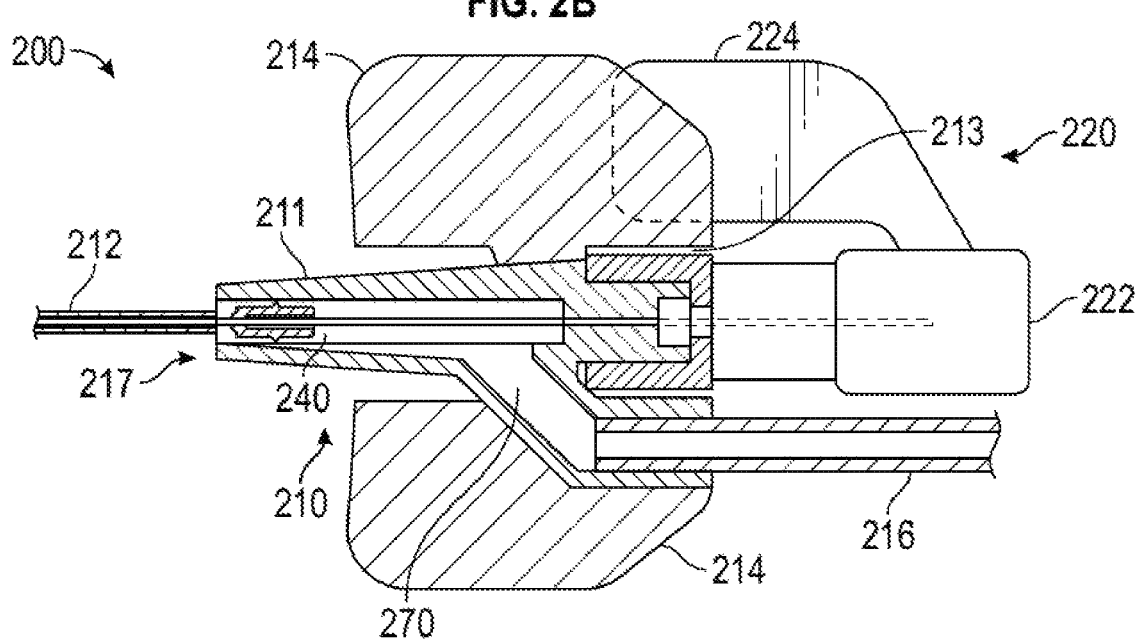
FIG. 2C is an enlarged cross-sectional side view of the catheter system shown in FIG. 2B.
Figures 3A, 3B:
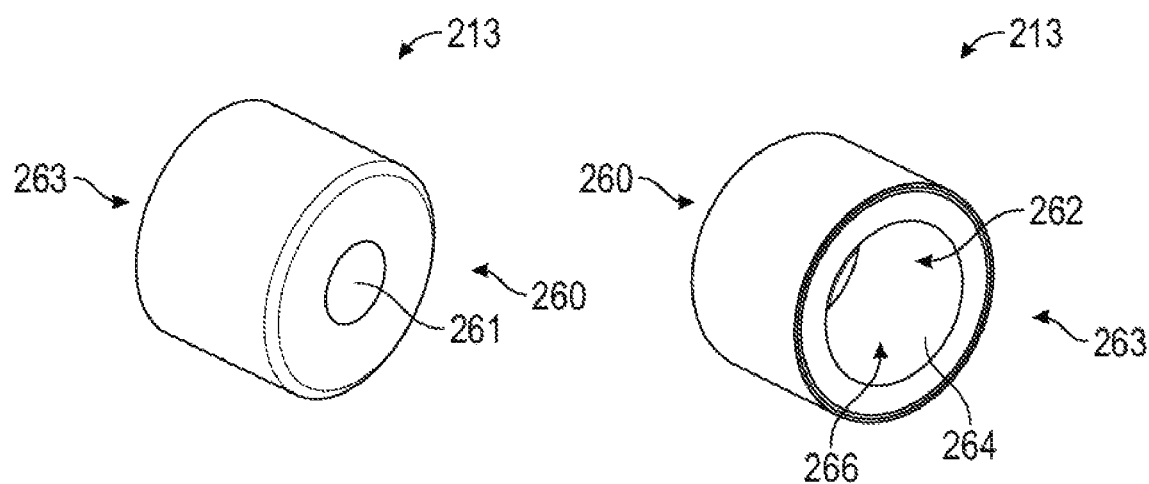
FIG. 3A is an isometric view of a proximal end of a compression cap, according to one embodiment of the present disclosure.
FIG. 3B is an isometric view of a distal end of the compression cap shown in FIG. 3A.
Figure 3C:
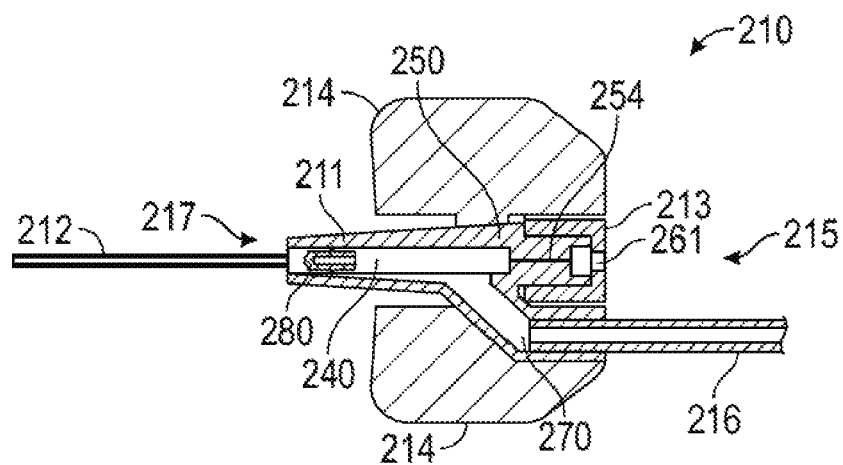
FIG. 3C is an enlarged cross-sectional side view of the catheter adapter of FIG. 2A without the needle component.

FIGS. 2A-2C and 3C illustrate various views of a catheter system 200 and a compliant catheter adapter 210, according to another embodiment of the present disclosure. FIGS. 3A and 3B illustrate a compression cap 213 that may be used with the compliant catheter adapter 210. FIG. 2A shows a needle component 220 removed from the compliant catheter adapter 210 and FIGS. 2B and 2C show the needle component 220 fully inserted into the compliant catheter adapter 210. FIG. 3C also shows the compliant catheter adapter 210 without the needle component 220. The needle component 220 may include a needle hub 222, a grip 224 coupled to the needle hub 222, and an elongate object, such as a needle 226, coupled to the needle hub 222. The needle component 220 embodiment shown in FIGS. 2A-2C and 3C illustrates a grip 224 having a paddle shape.

Continuing with FIGS. 2A-3C collectively, the compliant catheter adapter 210 may include a catheter adapter body 211 formed of a compliant material. The catheter adapter body 211 may be integrally formed from a compression set resistant elastomeric material such as a thermoplastic elastomer, a liquid silicone rubber, and a polyisoprene. In at least some embodiments, the catheter adapter body 211 may be substantially formed from a single compression set resistant elastomeric material. In at least one embodiment, the catheter adapter body 211 may be integrally manufactured from a compliant material to form an inner chamber 240, a port 270, a compression resistant septum 250 with a lumen 254 extending there through, a catheter wedge 280, and one or more stabilization members 214. The catheter adapter body 211 may also be coupled to any number of non-integral components including, but not limited to: a compression cap 213, a catheter lumen 212, and an extension tube 216.

The catheter adapter body 211 may have a proximal end 215 and a distal end 217. The catheter adapter body 211 may have a generally elongate shape formed about a longitudinal axis of the catheter adapter body 211 (not shown) extending between the proximal end 215 and the distal end 217 of the catheter adapter body 211. The inner chamber 240 may be disposed within the catheter adapter body 211 and also have a generally elongate shape formed about the longitudinal axis of the catheter adapter body 211. The inner chamber 240 may be in fluid communication with the catheter lumen 212. The inner chamber 240 may also include a catheter wedge 280, which may be integrally formed with the inner chamber 240, or may be separately formed from the inner chamber 240 and then coupled to the inner chamber 240. The catheter wedge 280 may be disposed toward the distal end 217 of the catheter adapter body 211 and configured to guide an elongate object into the catheter lumen 212 as the elongate object is inserted through the catheter adapter body 211. For example, the catheter wedge 280 may facilitate and/or guide insertion of the needle 226 into the catheter lumen 212.

The port 270 may be in fluid communication with the inner chamber 240 and configured to receive an extension tube 216. The port 270 shown in FIGS. 2A-2C and 3C has a portion that is generally forms a Y-shape in relation to the inner chamber 240 and another portion that generally runs parallel to the inner chamber 240. However, it is understood that the port 270 can be any suitable shape and size including, but not limited to: a Y-shaped port, a T-shaped port, a V-shaped port, a parallel-shaped port, etc.

The one or more stabilization members 214 may be coupled to the catheter adapter body 211 and configured to stabilize the catheter adapter body 211 with respect to a patient (not shown). In at least one embodiment, the one or more stabilization members 214 may be integrally formed with the catheter adapter body 211 such that they are formed from the same compliant material as the catheter adapter body 211. This may allow the catheter adapter body 211 to better conform to the patient's body, improve patient comfort, and improve fixation of the catheter adapter body 211 to the patient after the catheter lumen 212 has been inserted.

The compression resistant septum 250 may be integrally formed in the compliant material of the catheter adapter body 211 and disposed toward the proximal end 215 of the catheter adapter body 211. The compression resistant septum 250 may include a lumen 254 that is formed through the compression resistant septum 250 and configured to receive an elongate object therein, such as the needle 226. In at least one embodiment, the compression resistant septum 250 may be integrally formed of the same compression set resistant elastomeric material as the catheter adapter body 211.

The compression cap 213 may be coupled to the compression resistant septum 250 and the compression cap 213 may be configured to impart a compression force to the compression resistant septum 250, such that the lumen 254 of the compression resistant septum 250 narrows and seals when the elongate object is removed from the lumen 254. In some embodiments, the compression force comprises radial and axial compression forces. In at least one embodiment, the compression cap 213 may have a generally cylindrical shape. However, it will be understood that the compression cap 213 may include any number of suitable shapes that are configured to impart radial and axial compression forces. The compression cap 213 may have a proximal end 260 and a distal end 263. The proximal end 260 may have a first aperture 261 formed therein and configured to receive the elongate object there through. The distal end 263 may have a second aperture 262 configured to receive at least a portion of the catheter adapter body 211 and/or at least a portion of the compression resistant septum 250. The compression cap 213 may also include a compression surface 264 that extends intermediate the proximal end 260 and the distal end 263 of the compression cap 213. The compression surface 264 may enclose a hollow portion 266 formed in the compression cap 213. The hollow portion 266 may be configured to receive at least a portion of the compression resistant septum 250 therein, and the compression surface 264 may be configured to impart the radial and axial compression forces to the compression resistant septum 250, such that the lumen 254 of the compression resistant septum 250 narrows and seals when the elongate object is removed from the lumen 254. In at least one embodiment, the compression cap 213 is a separate piece that may be coupled to the compression resistant septum 250. However, in other embodiments the compression cap 213 may be integrally formed with the compression resistant septum 250. In yet other embodiments, the compression cap 213 may be coupled to the compression resistant septum 250 through an over-molding manufacturing process.

Figure 3D:
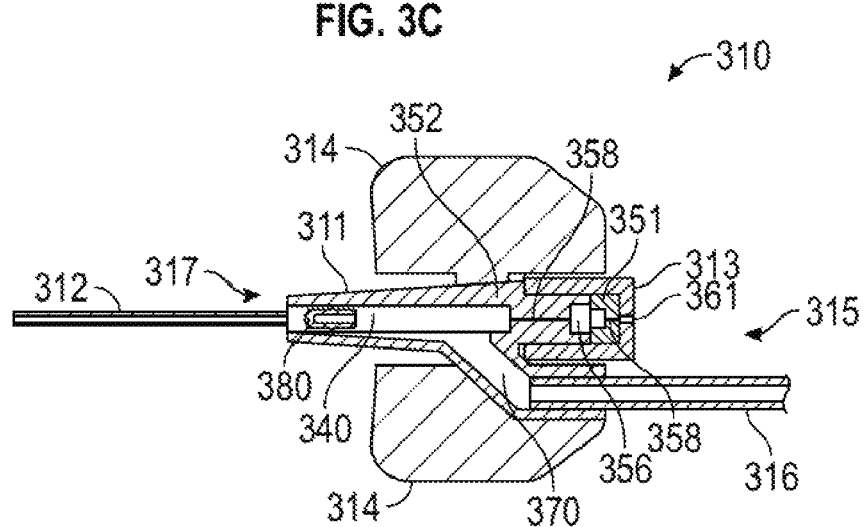
FIG. 3D is a cross-sectional side view of a catheter adapter, according to another embodiment of the present disclosure.

FIG. 3D shows a cross-sectional side view of a compliant catheter adapter 310, according to another embodiment of the present disclosure. The compliant catheter adapter 310 may include similar features to the compliant catheter adapter 210 of FIGS. 2A-2C and 3C, such as: a catheter adapter body 311 having a proximal end 315 and a distal end 317, a catheter lumen 312, a compression cap 313, one or more one or more stabilization members 314, an extension tube 316, an inner chamber 340, a port 370, and a catheter wedge 380. However, the compliant catheter adapter 310 may also include additional features, such as: a first compression resistant septum 351, a second compression resistant septum 352, a septum chamber 356 intermediate the first compression resistant septum 351 and the second compression resistant septum 352, a first lumen 357, and a second lumen 358.

The first compression resistant septum 351 may be positioned to abut at least a portion of the proximal end 315 of the catheter adapter body 311 and/or the second compression resistant septum 352. The first lumen 357 may be configured to receive an elongate object. The second compression resistant septum 352 may include a second lumen 358 formed there through which may also be configured to receive the elongate object. In at least some embodiments, the second compression resistant septum 352 may be disposed within the inner chamber 340 of the catheter adapter body 311. The second compression resistant septum 352 may be positioned to abut the first compression resistant septum 351 and the septum chamber 356 may be formed between the first compression resistant septum 351 and the second compression resistant septum 352. The compression cap 313 may be configured to couple the first compression resistant septum 351 to the catheter adapter body 311 and/or the second compression resistant septum 352. The compression cap 313 may also be configured to impart radial and axial compression forces to the first compression resistant septum 351 and/or the second compression resistant septum 352 such that the first lumen 357 and the second lumen 358 narrow and seal when the elongate object is removed from the first lumen 357 and the second lumen 358. This configuration may provide additional sealing capabilities and thus, additional safety.

Figure 4A:
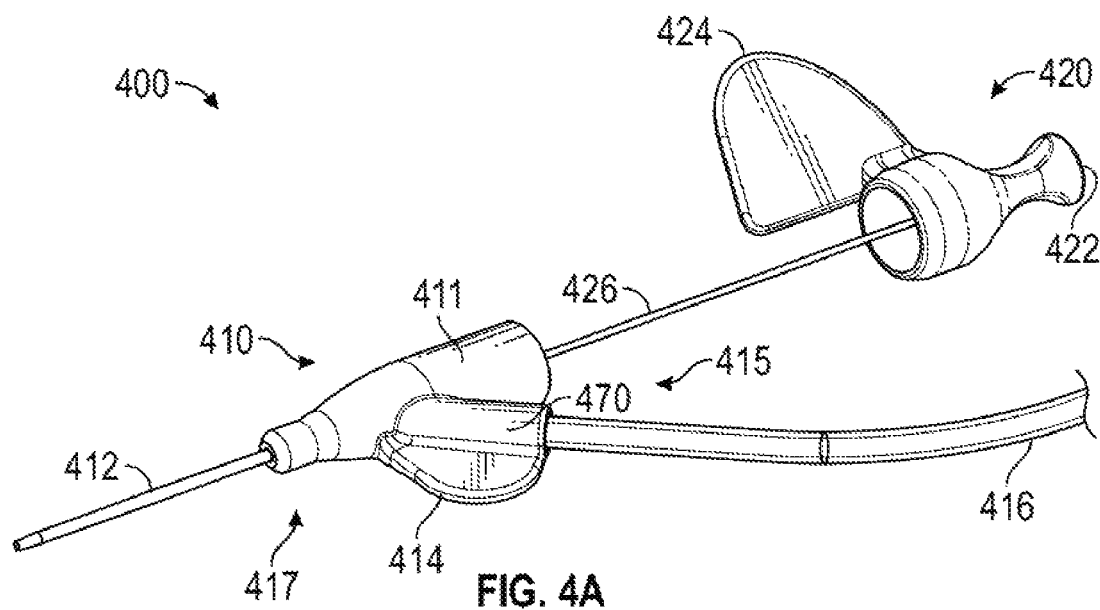
FIG. 4A is an isometric view of a catheter system with a needle component removed from a catheter adapter, according to another embodiment of the present disclosure.
Figure 4B:
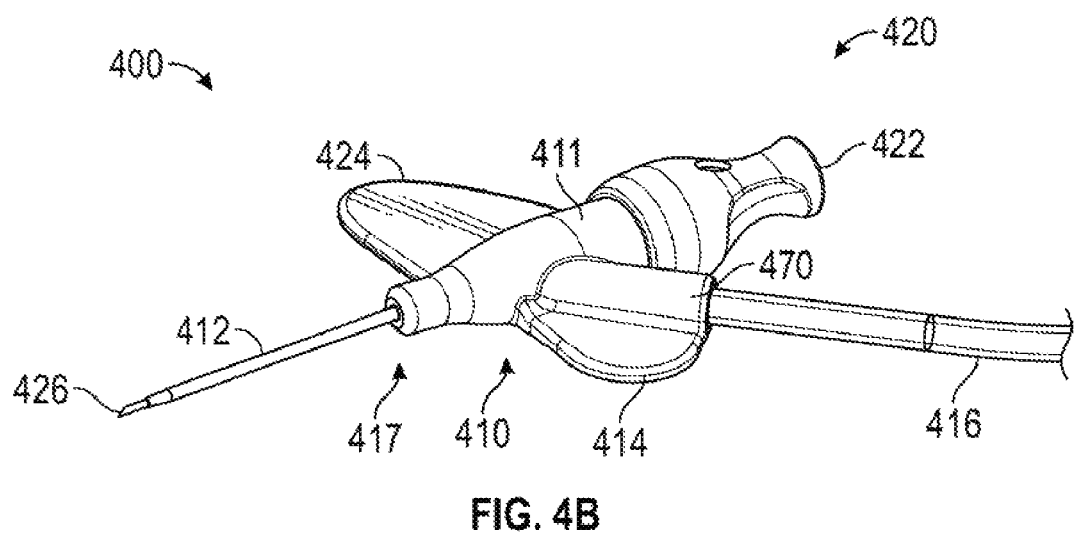
FIG. 4B is an isometric view of the catheter system of FIG. 4A with the needle component fully inserted into the catheter adapter and rotated to a first position.
Figure 4C:
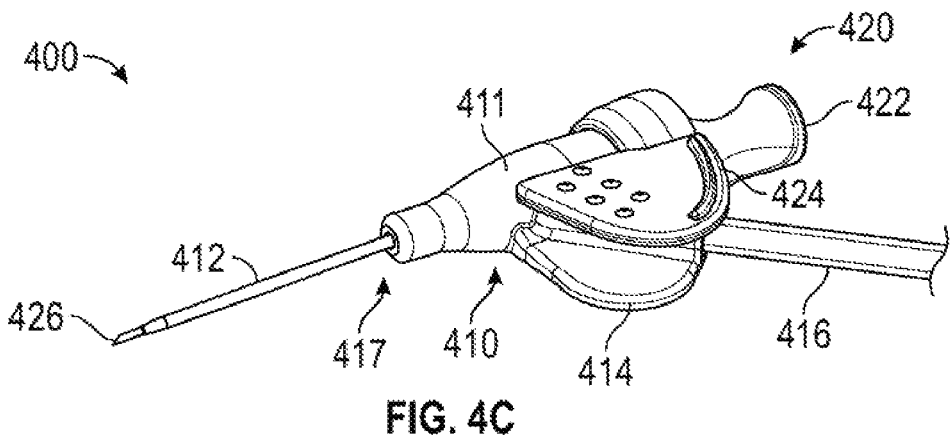
FIG. 4C is an isometric view of the catheter system of FIG. 4A with the needle component fully inserted into the catheter adapter and rotated to a second position.
Figure 5:
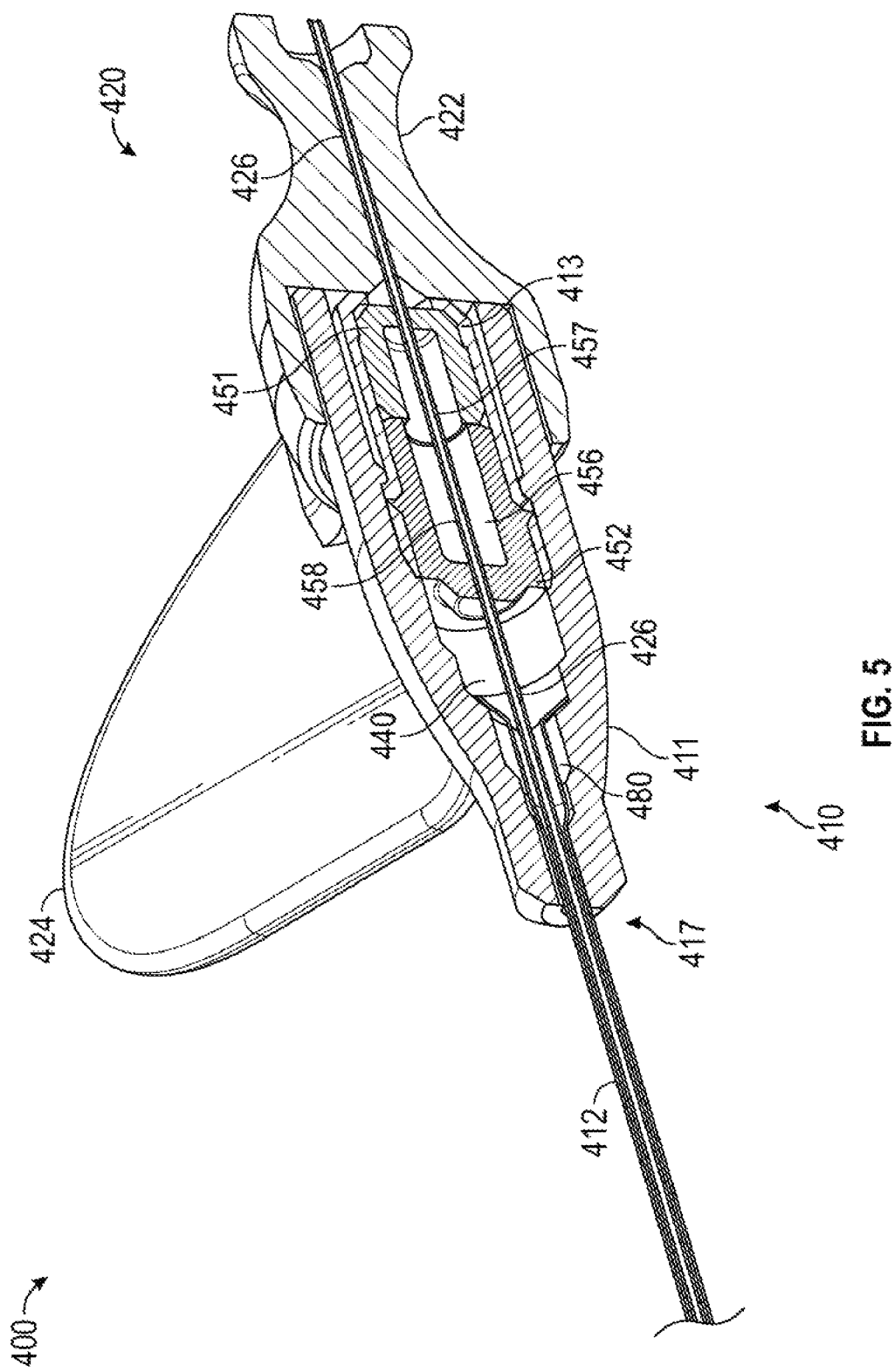
FIG. 5 is a cross-sectional isometric view of the catheter system of FIG. 4B.
Figure 6A:
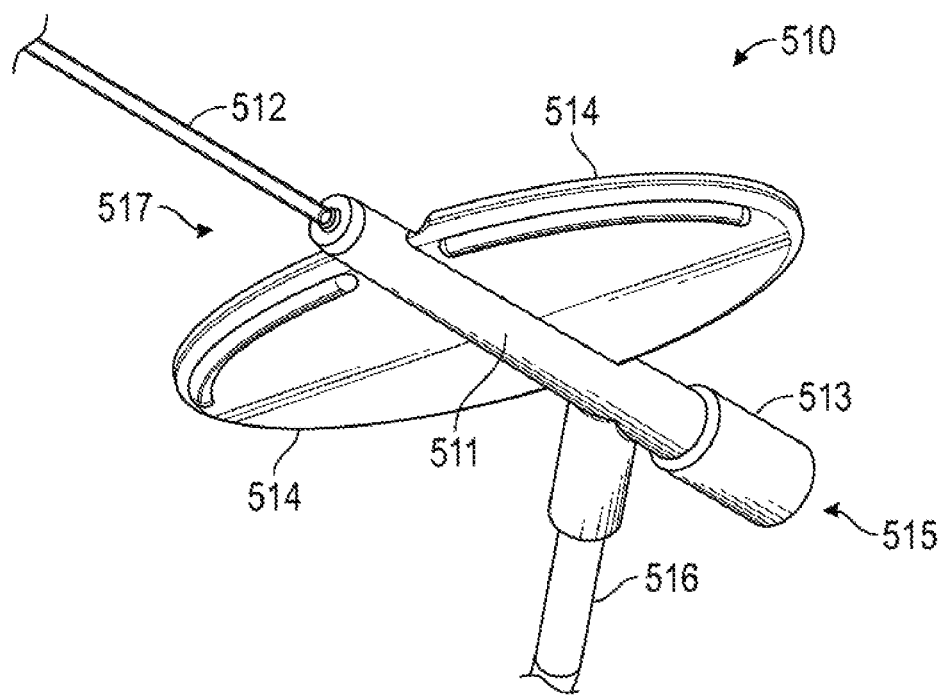
FIG. 6A is an isometric bottom view of a catheter adapter, according to another embodiment of the present disclosure.
Figure 6B:
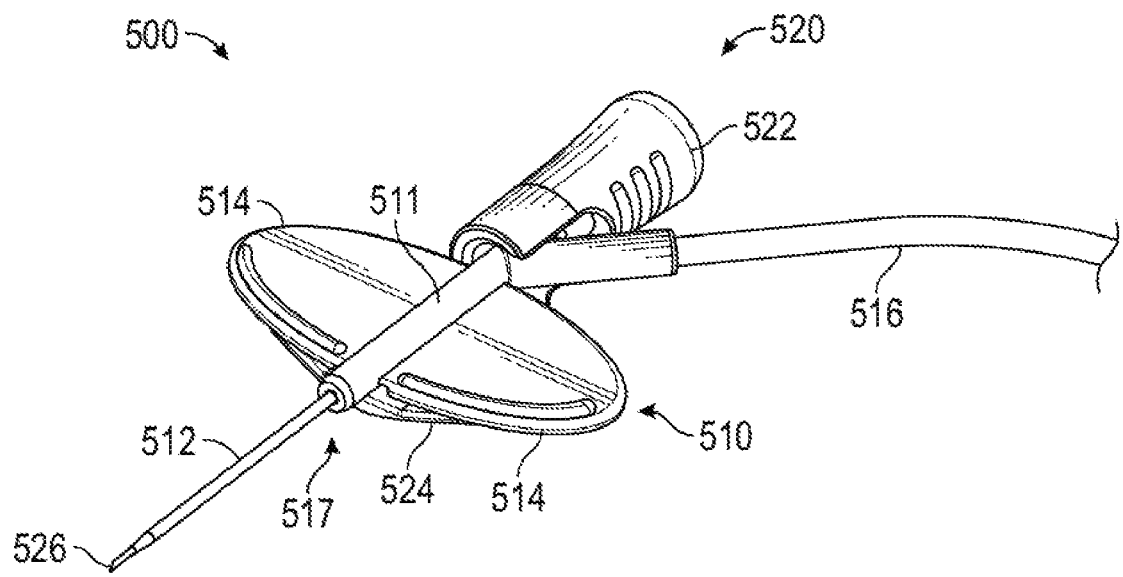
FIG. 6B is an isometric top view of a catheter system including the catheter adapter of FIG. 6A and a needle component fully inserted into the catheter adapter.

FIGS. 4A-5 illustrate various views of a catheter system 400, according to another embodiment of the present disclosure. FIGS. 4A-4C show the catheter system 400 with a needle component 420 in various positions relative to a compliant catheter adapter 410 and FIG. 5 shows a cross-sectional view of the catheter system 400 of FIG. 4B. The catheter system 400 may include similar features to other catheter system described herein, such as: a catheter adapter body 411 having a proximal end 415 and a distal end 417, a catheter lumen 412, a compression cap 413, one or more stabilization members 414, an extension tube 416, an inner chamber 440, a port 470, a catheter wedge 480, a needle hub 422, a grip 424, and a needle 426. Furthermore, as can be seen in FIG. 5, the catheter system 400 may also include a first compression resistant septum 451, a second compression resistant septum 452, a septum chamber 456 intermediate the first compression resistant septum 451 and the second compression resistant septum 452, a first lumen 457, and a second lumen 458. In some instances, second compression resistant septum 452 may be termed the primary or high pressure septum, and first compression resistant septum 451 may be termed the low pressure or secondary septum.

The first compression resistant septum 451 may be positioned to abut at least a portion of the proximal end 415 of the catheter adapter body 411 and/or the second compression resistant septum 452. The first lumen 457 may be configured to receive an elongate object. The second compression resistant septum 452 may include a second lumen 458 formed there through which may also be configured to receive the elongate object. In at least some embodiments, the second compression resistant septum 452 may be disposed within the inner chamber 440 of the catheter adapter body 411. The second compression resistant septum 452 may be positioned to abut the first compression resistant septum 451 and the septum chamber 456 may be formed between the first compression resistant septum 451 and the second compression resistant septum 452. The compression cap 413 may be configured to couple the first compression resistant septum 451 to the catheter adapter body 411 and/or the second compression resistant septum 452. The compression cap 413 may also be configured to impart radial and axial compression forces to the first compression resistant septum 451 and/or the second compression resistant septum 452 such that the first lumen 457 and/or the second lumen 458 narrow and seal when the elongate object is removed from the first lumen 457 and/or the second lumen 458. In at least one embodiment, the compression cap 413, the first compression resistant septum 451, and/or the second compression resistant septum 452 may be positioned within the proximal end 415 of the catheter adapter body 411, as can be seen in FIG. 5.

Figure 7A:
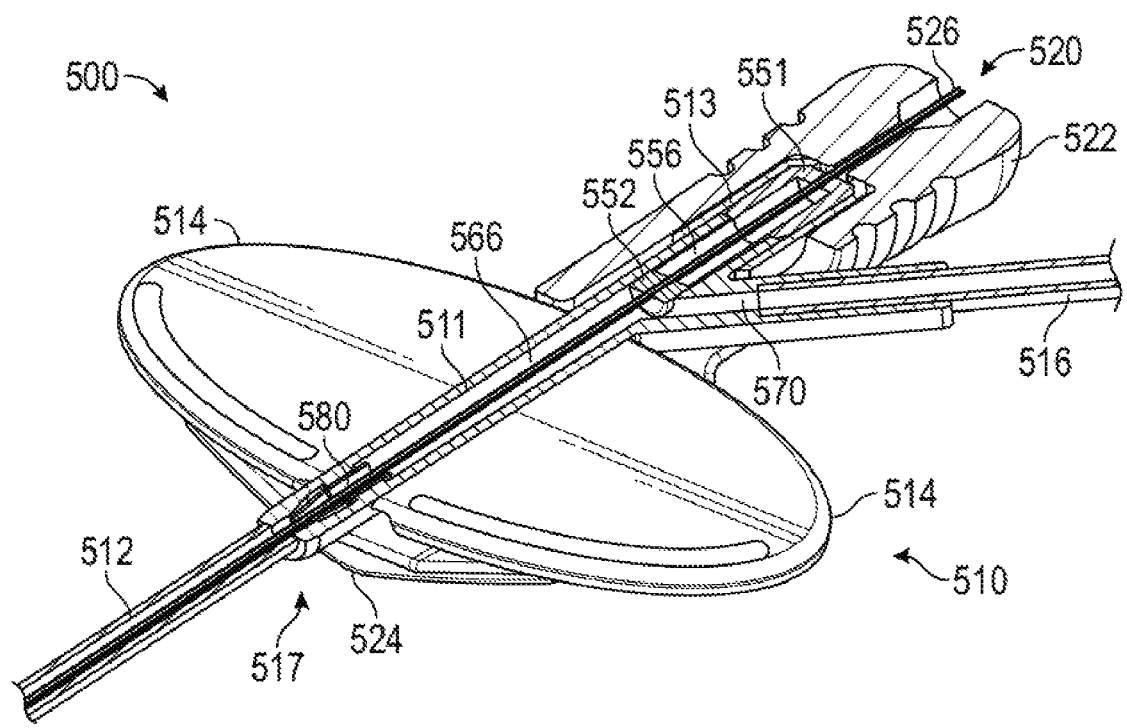
FIG. 7A is a cross-sectional isometric view of the catheter system of FIG. 6B.
Figure 7B:
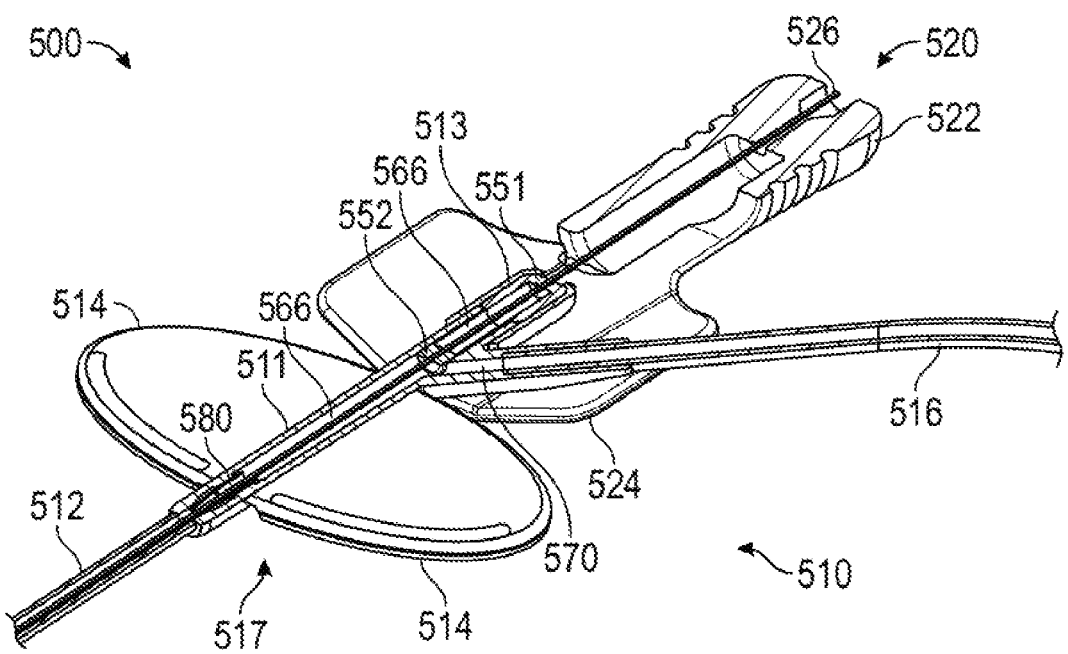
FIG. 7B is a cross-sectional isometric view of the catheter system of FIG. 6B with the needle component partially removed from the catheter adapter.
Figure 8:
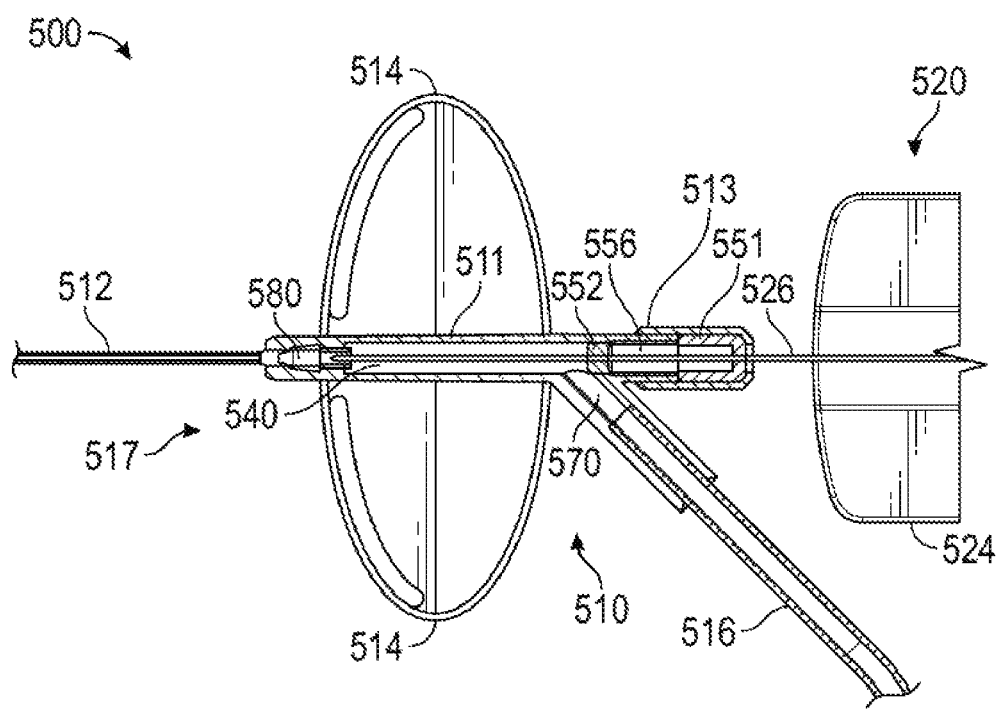
FIG. 8 is a cross-sectional top view the catheter system of FIG. 6B with the needle component partially removed from the catheter adapter.

FIGS. 6A-8 illustrate various views of a catheter system 500, according to another embodiment of the present disclosure. The catheter system 500 may include similar features to other catheter system described herein, such as: a catheter adapter body 511 having a proximal end 515 and a distal end 517, a catheter lumen 512, a compression cap 513, one or more one or more stabilization members 514, an extension tube 516, an inner chamber 540, a port 570, a catheter wedge 580, a needle hub 522, a grip 524, and a needle 526. Furthermore, as can be seen in FIGS. 7A-8, the catheter system 500 may also include a first compression resistant septum 551 with a first lumen formed there through, a second compression resistant septum 552 with a second lumen formed there through, and a septum chamber 556 intermediate the first compression resistant septum 551 and the second compression resistant septum 552.

The first compression resistant septum 551 may be positioned to abut at least a portion of the proximal end 515 of the catheter adapter body 511 and/or the second compression resistant septum 552. The first and second lumens may be configured to receive an elongate object. In at least some embodiments, the second compression resistant septum 552 may be disposed within the inner chamber 540 of the catheter adapter body 511. The second compression resistant septum 552 may be positioned to abut the first compression resistant septum 551 and the septum chamber 556 may be formed between the first compression resistant septum 551 and the second compression resistant septum 552. The compression cap 513 may be configured to couple the first compression resistant septum 551 to the catheter adapter body 511 and/or the second compression resistant septum 552. The compression cap 513 may also be configured to impart radial and axial compression forces to the first compression resistant septum 551 and/or the second compression resistant septum 552 such that the first lumen and the second lumen narrow and seal when the elongate object is removed from the first lumen and the second lumen.

Figure 9A:
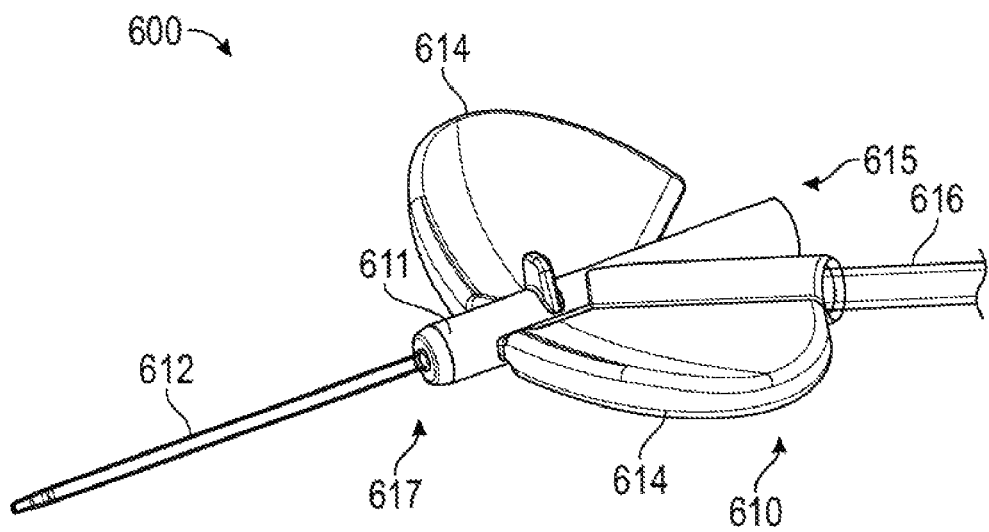
FIG. 9A is an isometric view of a catheter system with a needle component removed from a catheter adapter, according to another embodiment of the present disclosure.
Figure 9B:
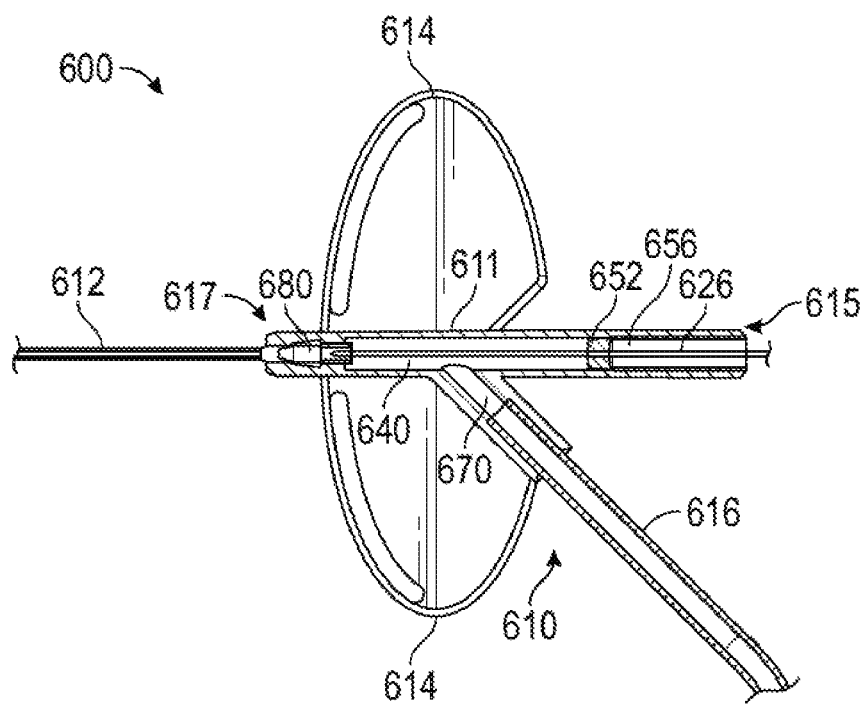
FIG. 9B is a cross-sectional top view of the catheter system of FIG. 9A.

FIGS. 9A and 9B illustrate two views of a catheter system 600, according to another embodiment of the present disclosure. The catheter system 600 may include similar features to other catheter system described herein, such as: a compliant catheter adapter 610 including a catheter adapter body 611 having a proximal end 615 and a distal end 617, a catheter lumen 612, a compression cap, one or more one or more stabilization members 614, an extension tube 616, an inner chamber 640, a port 670, and a catheter wedge 680. The catheter system 600 may also have a needle component including a needle hub, a grip, and a needle 626. Furthermore, the catheter system 600 may also include a first compression resistant septum with a first lumen formed there through, a second compression resistant septum 652 with a second lumen formed there through, and a septum chamber 656 intermediate the first compression resistant septum and the second compression resistant septum 652.

The first compression resistant septum may be positioned to abut at least a portion of the proximal end 615 of the catheter adapter body 611 and/or the second compression resistant septum 652. The first and second lumens may be configured to receive an elongate object. In at least some embodiments, the second compression resistant septum 652 may be disposed within the inner chamber 640 of the catheter adapter body 611. The second compression resistant septum 652 may be positioned to abut the first compression resistant septum and the septum chamber 656 may be formed between the first compression resistant septum and the second compression resistant septum 652. The compression cap may be configured to couple the first compression resistant septum to the catheter adapter body 611 and/or the second compression resistant septum 652. The compression cap may also be configured to impart radial and axial compression forces to the first compression resistant septum and/or the second compression resistant septum 652 such that the first lumen and the second lumen narrow and seal when the elongate object is removed from the first lumen and the second lumen.

FIGS. 10A-10G illustrate another catheter system 700, according to some embodiments. In some embodiments, the catheter system 700 may include similar features to other catheter systems described in the present disclosure, such as: a compliant catheter adapter that includes a catheter adapter body 704 having a proximal end 706 and a distal end 708, a catheter lumen 710, a compression cap 712, one or more stabilization members 714, an extension tube 716, an inner chamber 718, a port 720, a catheter wedge 722, a needle hub 724, a grip 726, a needle 728, a first compression resistant septum 732, a second compression resistant septum 734, and a septum chamber 736 intermediate the first compression resistant septum 732 and the second compression resistant septum 734.

Figure 10A:
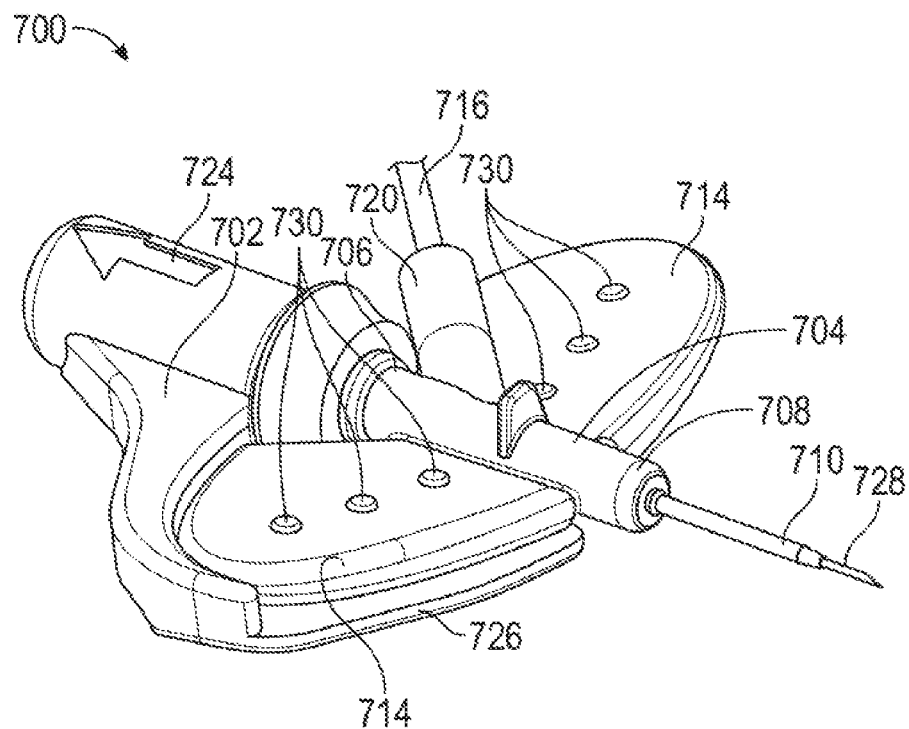
FIG. 10A is an upper perspective view of a catheter system with a needle component fully inserted into a catheter adapter of the catheter system, according to some embodiments.
Figure 10B:
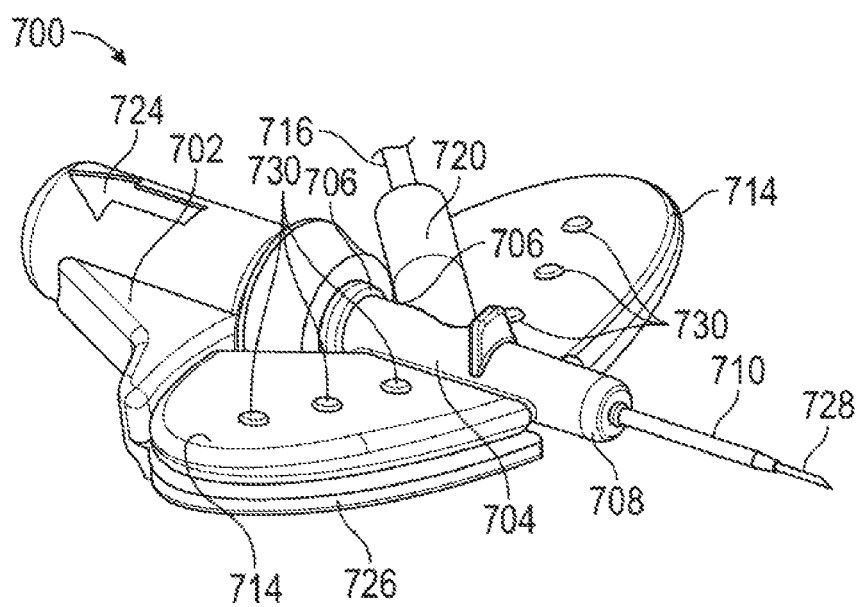
FIG. 10B is an upper perspective view of the catheter system of FIG. 10A with the needle component fully inserted into the catheter adapter, according to some embodiments.
Figure 10C:
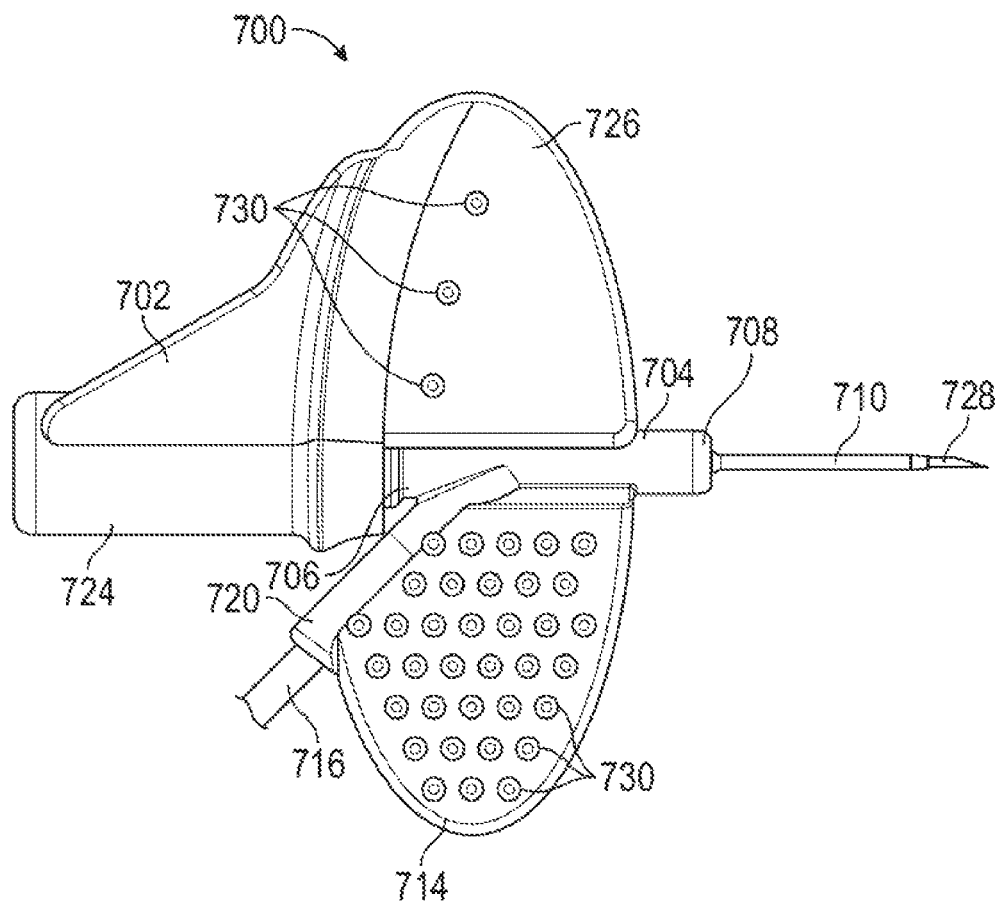
FIG. 10C is a bottom view of the catheter system of FIG. 10A with the needle component fully inserted into the catheter adapter, according to some embodiments.
Figure 10D:
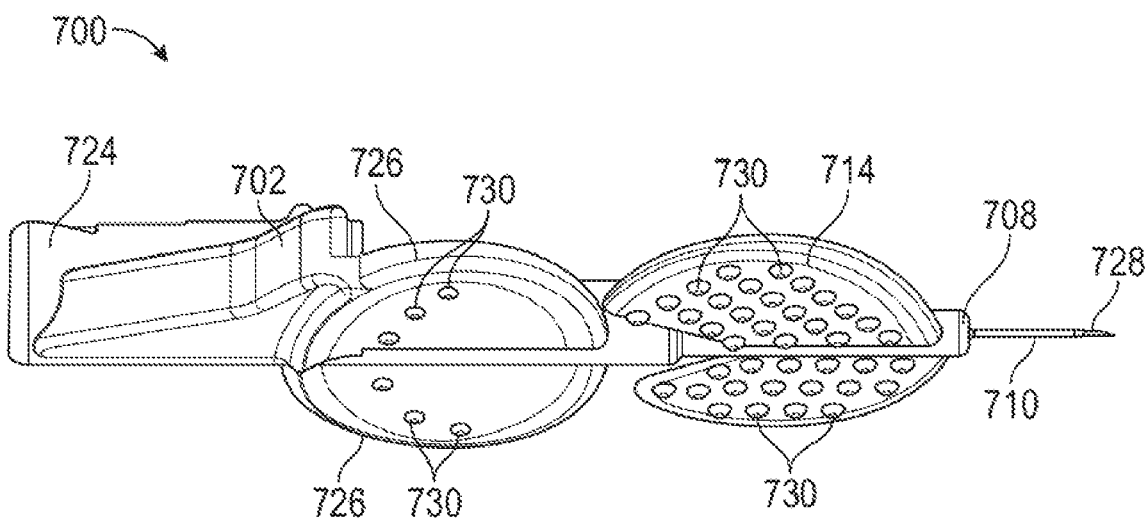
FIG. 10D is a lower perspective view of the catheter system of FIG. 10A with the needle component partially removed from the catheter adapter, according to some embodiments.
Figure 10E:
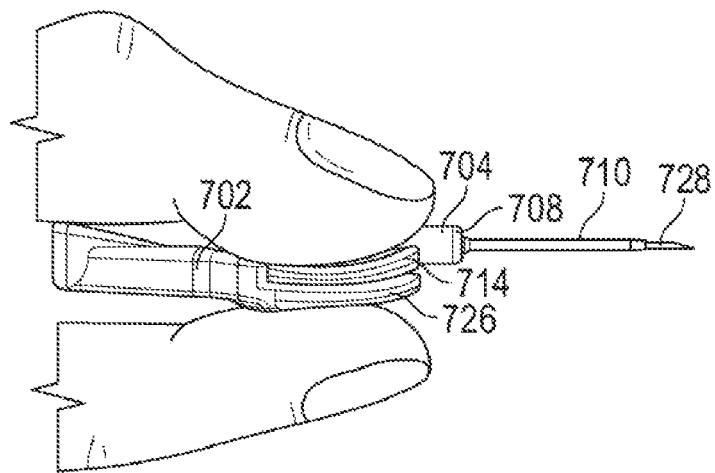
FIG. 10E illustrates the catheter system of FIG. 10A being gripped by a clinician, according to some embodiments.
Figure 10F:
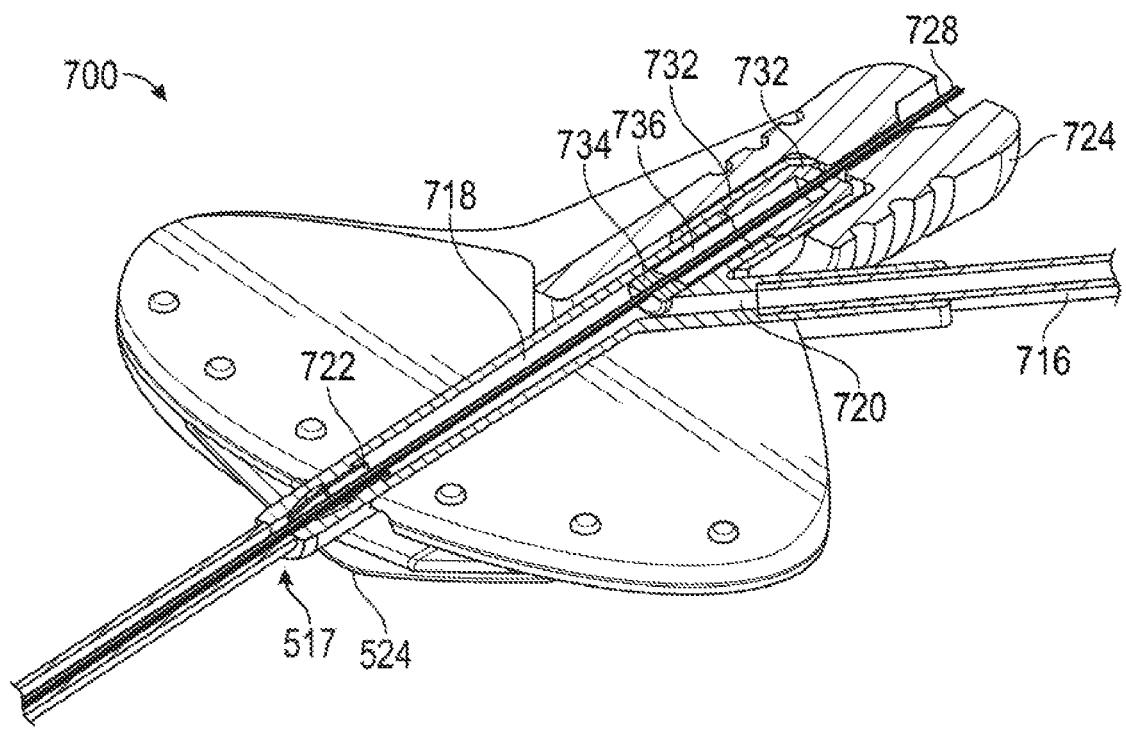
FIG. 10F is a partial cutaway view of the catheter system of FIG. 10A with the needle component fully inserted into the catheter adapter, according to some embodiments.
Figure 10G:
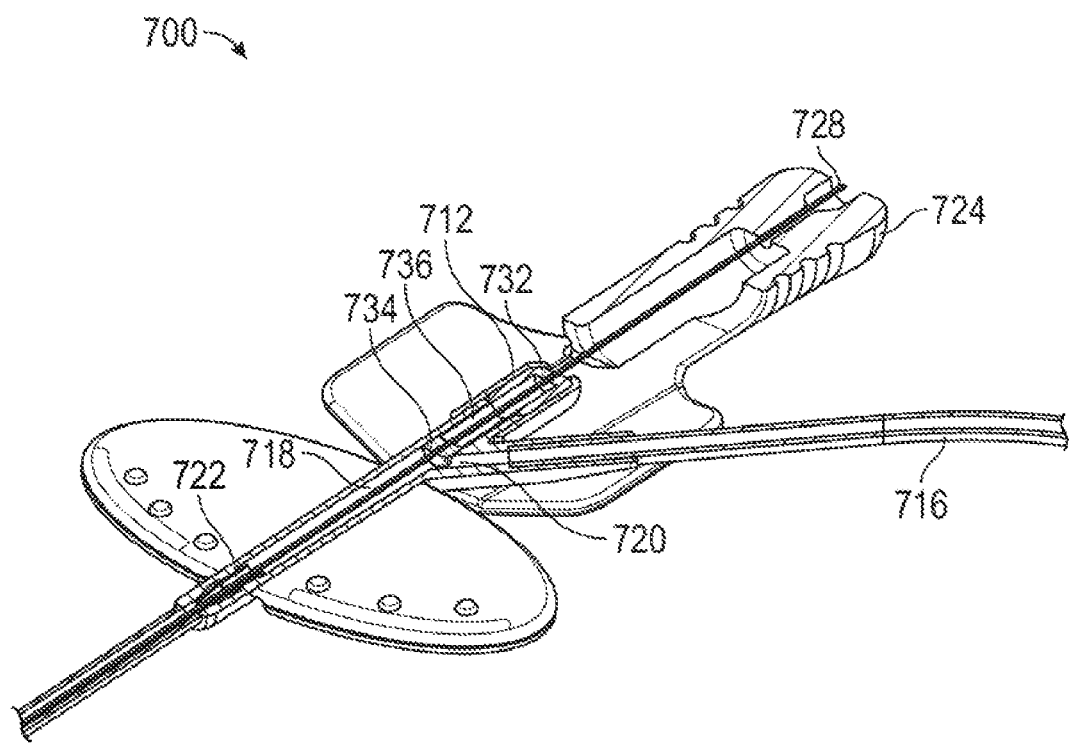
FIG. 10G is a partial cutaway view of the catheter system of FIG. 10A with the needle component partially removed from the catheter adapter, according to some embodiments.

Furthermore, as can be seen in FIGS. 10A-10F, in some embodiments, the catheter system 700 may include one or more protrusions or bumps 730 that may increase friction and aid in gripping of the stabilization members 714 and/or the grip 726, as illustrated, for example, in FIG. 10E. In some embodiments, the bumps 730 may facilitate breathing of skin of the patient that contacts the stabilization members 714 and/or the grip 726. The bumps 730 may be arranged in any number of patterns. For example, multiple of the bumps 730 may be evenly spaced apart and/or may be arranged in rows. In some embodiments, the bumps 730 on a surface of the stabilization members 714 and/or on a surface of the grip 726 may be arranged in a single row or arc. The bumps 730 may include any number of shapes. For example, the bumps 730 may be circular, oval, square, etc.

Furthermore, in some embodiments, the catheter system 700 may include a support element 702 that may support a finger or thumb of the clinician and/or facilitate gripping of the catheter system 700 by the finger or the thumb, as illustrated, for example, in FIG. 10E. In some embodiments, the support element 702 may extend upwardly from the grip 726 to a height equal to or greater than a height of the stabilization members 714. Thus, in some embodiments, a diameter of the support element 702 may be equal to or greater than a diameter of the stabilization members 714. In some embodiments, the support element 702 may be coupled with the needle hub 724 and/or the grip 726. In some embodiments, the support element 702 may be integrally formed with the needle hub 724 and/or the grip 726. In some embodiments, the catheter system 700 may include multiple support elements 702, which may be disposed on opposing sides of the catheter system 700.

In some embodiments, a color contrast between the support element 702 and one or more of the stabilization members 714 may be provided. For example, the support element may include a translucent or a white color, while the stabilization members 714 may include a different color than the support element such as, for example, green, pink, blue, yellow, purple, etc. In some embodiments, a color of the stabilization members 714 may correspond to a gauge size of a catheter of the catheter system 700. The color contrast may facilitate identification by the clinician of parts of the catheter system 700 that separate from one another during insertion of the catheter system 700 into the vein of the patient, including, for example, hooding of the catheter.

In some embodiments, the support element 702 may extend along at least a portion of an edge of a particular stabilization member 714. As illustrated in FIG. 10A, in some embodiments, the support element 702 may extend to a side of the particular stabilization member 714 and/or a side of the grip 726. As illustrated in FIG. 10B, in some embodiments, the support element 702 may extend along a proximal end of the particular stabilization member 714 and/or a proximal end of the grip 726. In some embodiments, a curvature of an inner edge of the support element 702 may correspond to a curvature of the grip 726.

In some embodiments, when the catheter system 700 is gripped as illustrated in FIG. 10E, the bumps 730 may contact the finger and/or the thumb of the clinician. In some embodiments, if the thumb, in contact with an upper surface of a particular stabilization member 714, is advanced distally while a forefinger, in contact with a lower surface of the grip 726, is retracted proximally, the catheter may be hooded and/or advanced for insertion of the catheter in a vein of the patient. When the catheter is hooded, a tip of the needle 728 may be fully encapsulated by the catheter.

In some embodiments, the needle hub 724 may include a flash chamber that may be coupled to a proximal end of the needle hub 724. In some embodiments, the flash chamber may provide secondary confirmation that the catheter is properly positioned within the vein. In some embodiments, because a proximal end of the needle 728 opens into the flash chamber and because the flash chamber may be vented to an external environment, blood pressure of the patient may cause blood to flow into the flash chamber.

Various embodiments of the present invention may further comprise a safety mechanism configured to secure the sharpened, distal tip of the introducer needle following removal and separation of the needle component from the catheter adapter. A safety mechanism may include any compatible device known in the art. In some instances, the safety mechanism is configured to interact with a needle feature, such as a ferrule, notch, crimp or bump on the needle. The crimp or bump formed in the needle cause a slight out of round configuration that can be used to activate a safety mechanism. In some instance, the safety mechanism comprises an arm or lever that is actuated to capture the needle tip within the mechanism and prevent the tip from emerging prior to safe disposal.

The safety mechanism is attached to the body of the needle and is capable of sliding along the length thereof. In some instances, an initial or assembled position of the safety mechanism is located in proximity to the base or proximal end of the needle component prior to catheterization. For some configurations, the assembled position of the safety mechanism is between the proximal end of the needle hub and the proximal end of the catheter adapter body or stabilization member(s), wherein the safety mechanism does not overlap the catheter adapter body or stabilization member(s). In some instances, a portion of the safety mechanism is positioned within the catheter adapter body, with the balance of the safety mechanism being positioned external to the catheter adapter body, such as within the needle hub. In some embodiments, a portion of the catheter adapter body or stabilization member(s) is extended proximally to provide a housing in which at least a portion of the safety mechanism is housed. In some instances, the entire safety mechanism is housed within the housing of the catheter adapter body or stabilization member(s) prior to catheterization.

In some embodiments, the assembled position of the safety mechanism positions the proximal end of the catheter adapter body between the distal end of the safety mechanism and a distal end of a grip of the needle component. In some instances, the assembled position of the safety mechanism positions the proximal end of the catheter adapter body between the distal end of the safety mechanism and a proximal end of a grip of the needle component. In some instances, a portion of the safety mechanism overlaps a portion of a grip of the needle component. In some embodiments, at least some portion of at least one of the catheter adapter body and the grip overlaps at least some portion of the safety mechanism. In some embodiments, no portion of the catheter adapter body or grip overlaps any portion of the safety mechanism.

In some embodiments, a defeatable mechanical connection is provided between the safety mechanism and at least one other component of the IV catheter system. In some embodiments, a distal end of the safety mechanism is selectively coupled to a proximal end of the catheter adapter body. In one embodiment, the safety mechanism interlocks internally to the proximal end of the catheter adapter body. In one embodiment, the safety mechanism interlocks externally to the proximal end of the catheter adapter body. In some embodiments, a distal end of the safety mechanism is selectively coupled to a proximal end of the stabilization member(s). In some embodiments, a surface of the safety mechanism is selectively coupled to at least one surface of at least one of the catheter adapter body, a blood control valve, an extension tube, and the stabilization member(s). In some instances, the mechanical connection is defeated upon securement of the needle tip within the safety mechanism.

In some embodiments, a particular catheter device, such as, for example, the catheter device of any of the FIGS. 1-10, may include a needle safety mechanism. The safety mechanism may include any safety mechanism configured to secure a sharpened, distal tip of an introducer needle when the needle is withdrawn from a catheter of the particular catheter device, preventing accidental needle sticks.

The safety mechanism may be coupled with the particular catheter device in any number of ways. In some embodiments, the safety mechanism may include an internal interlock in which the safety mechanism is coupled with an internal surface of a catheter adapter. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety. In some embodiments, the safety mechanism may include a clip disposed within the catheter adapter, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled with an external surface of the catheter adapter. In some embodiments, the safety mechanism may be coupled with an external surface of the catheter adapter and an internal and/or external surface of a needle hub. Coupling may include threading, fitting, snapping, connecting, attaching, fastening, clipping, hooking, or any other suitable means of coupling. Non-limiting examples of safety mechanisms that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter adapter.

In some embodiments, a defeatable mechanical connection is provided between the safety mechanism and at least one other component of the IV catheter system. In some instances, the mechanical connection is defeated upon securement of the distal tip of the needle within the safety mechanism. In some embodiments, a surface of the safety mechanism is selectively coupled to one or more of the following: the catheter adapter, a blood control valve, an extension tube, and one or more paddle grips.

In some embodiments, the safety mechanism may include a safety barrel, which may be spring-loaded. For example, the safety barrel may be spring loaded as in the BD™ Insyte® Autoguard™ BC shielded protective IV catheter. In some embodiments, the safety mechanism may be passively and/or actively activated. In some embodiments, the safety mechanism may be configured to interact with a needle feature, such as a ferrule, notch, crimp or bump on the needle. In some embodiments, the safety mechanism may include an arm or lever that may be actuated to capture the distal tip within the safety mechanism and prevent the tip from emerging prior to safe disposal. In some embodiments, the safety mechanism may be attached to a body of the needle and may be capable of sliding along the length thereof.

In some embodiments, in an assembled position prior to catheterization, the safety mechanism may be disposed between the catheter adapter and the needle hub. In some embodiments, the catheter adapter and the needle hub may be spaced apart by at least a portion of the safety mechanism in the assembled position prior to catheterization. In some embodiments, in the assembled position prior to catheterization, a proximal end of the catheter adapter may be disposed between a distal end of the safety mechanism and a distal end of a grip of the needle hub, such as, for example, a paddle grip. In some embodiments, in the assembled position prior to catheterization, the proximal end of the catheter adapter body may be disposed between the distal end of the safety mechanism and a proximal end of the grip of the needle hub. In some embodiments, a portion of the safety mechanism may overlap with a portion of the grip of the needle hub. In some embodiments, at least a portion of at least one of the catheter adapter and the grip overlaps at least some portion of the safety mechanism. In some embodiments, no portion of the catheter adapter body or the grip overlaps any portion of the safety mechanism.

The present disclosure may be embodied in other specific forms without departing from its structures, methods, or other essential characteristics as broadly described herein and claimed hereinafter. The described embodiments are to be considered in all respects only as illustrative, and not restrictive. The scope of the present disclosure is, therefore, indicated by the appended claims, rather than by the foregoing description. All changes that come within the meaning and range of equivalency of the claims are to be embraced within their scope.

What is claimed is:

1. A compliant catheter adapter comprising:
    a catheter adapter body formed of a compliant material, the catheter adapter body comprising:
        a proximal end and a distal end, the catheter adapter body having a generally elongate shape formed about a longitudinal axis extending between the proximal end and the distal end of the catheter adapter body; and
        an inner chamber disposed within the catheter adapter body, the inner chamber having a generally elongate shape formed about the longitudinal axis extending between the proximal end and the distal end of the catheter adapter body;
    a first compression resistant septum positioned to abut at least a portion of the proximal end of the catheter adapter body, the first compression resistant septum comprising a first lumen formed therethrough and configured to receive an elongate object;
    a second compression resistant septum disposed within the inner chamber of the catheter adapter body, wherein a septum chamber is formed between the first compression resistant septum and the second compression resistant septum; and
    a compression cap configured to couple the first compression resistant septum to the catheter adapter body and impart a compression force to the first compression resistant septum such that the first lumen narrows and seals when the elongate object is removed from the first lumen.

2. The compliant catheter adapter of claim 1, wherein the catheter adapter body is integrally formed from a compression set resistant elastomeric material comprising one of a thermoplastic elastomer material, a liquid silicone rubber material, and a polyisoprene material.

3. The compliant catheter adapter of claim 1, wherein the compression cap is positioned within at least a portion of the proximal end of the catheter adapter body, the compression cap further comprising:
    a proximal end having a first aperture configured to receive the elongate object there through;
    a distal end having a second aperture configured to receive at least a portion of the catheter adapter body; and
    a compression surface extending intermediate the proximal end and the distal end of the compression cap, the compression surface enclosing a hollow portion formed in the compression cap, the hollow portion configured to receive the first compression resistant septum therein, and the compression surface configured to impart the compression force to the first compression resistant septum such that the first lumen narrows and seals when the elongate object is removed from the first lumen.

4. The compliant catheter adapter of claim 1, further comprising:
    one or more stabilization members coupled to the catheter adapter body and configured to stabilize the catheter adapter body with respect to a patient;
    a port in fluid communication with the inner chamber and configured to receive an extension tube, and the port comprising one of a Y-shaped port, a T-shaped port, a V-shaped port, and a parallel-shaped port;
    a catheter lumen coupled to and extending from the distal end of the catheter adapter body; and
    a catheter wedge disposed toward the distal end of the catheter adapter body and configured to guide the elongate object into the catheter lumen as the elongate object is inserted through the catheter adapter body.

5. The compliant catheter adapter of claim 1, wherein the second compression resistant septum is positioned to abut the first compression resistant septum.

6. The compliant catheter adapter of claim 5, wherein the second compression resistant septum comprises a second lumen formed therethrough and configured to receive the elongate object.

7. The compliant catheter adapter of claim 1, wherein the compression cap is a separate piece that is coupled to the first compression resistant septum and the catheter adapter body.

8. The compliant catheter adapter of claim 1, wherein the compression cap is coupled to the first compression resistant septum and the catheter adapter body through an overmolding manufacturing process.

9. The compliant catheter adapter of claim 1, further comprising a septum chamber intermediate the first compression resistant septum and a second compression resistant septum.

10. A catheter system comprising:
    a needle component including:
        a needle hub;
        a needle coupled to the needle hub and extending distally from the needle hub; and a grip coupled to the needle hub;
a catheter adapter body formed of a compliant material, the catheter adapter body comprising:
- a proximal end and a distal end, the catheter adapter body having a generally elongate shape formed about a longitudinal axis extending between the proximal end and the distal end of the catheter adapter body;
- an inner chamber disposed within the catheter adapter body, the inner chamber having a generally elongate shape formed about the longitudinal axis extending between the proximal end and the distal end of the catheter adapter body; and
- a first compression resistant septum and a second compression resistant septum formed in the compliant material of the catheter adapter body, wherein the first compression resistant septum is disposed toward the proximal end of the catheter adapter body and comprises a first lumen formed therethrough and configured to receive the needle therein; and a compression cap coupled to at least one of the first compression resistant septum and the second compression resistant septum, the compression cap configured to impart a compression force to the first compression resistant septum such that the lumen narrows and seals when the needle is removed from the lumen.

11. The catheter system of claim 10, wherein the grip coupled to the needle hub further comprises one of a paddle grip, a straight grip, and a ported grip.

12. The catheter system of claim 11, wherein the grip comprises a plurality of protrusions or bumps to increase friction of the grip.

13. The catheter system of claim 10, further comprising:
- one or more stabilization members coupled to the catheter adapter body and configured to stabilize the catheter adapter body with respect to a patient; and
- a port in fluid communication with the inner chamber and configured to receive an extension tube.

14. The catheter system of claim 13, wherein the needle hub is disposed adjacent to the catheter adapter body such that the grip is positioned atop the one or more stabilization members.

15. The catheter system of claim 14, wherein the needle hub comprises a cutout portion configured to receive the port.

16. The catheter system of claim 13, wherein the one or more stabilization members comprises a plurality of protrusions or bumps to increase friction of the one or more stabilization members.

17. The catheter system of claim 13, wherein the port comprises one of a Y-shaped port, a T-shaped port, a V-shaped port, and a parallel-shaped port.

18. The catheter system of claim 10, wherein the compression resistant septum comprises a first compression resistant septum and a second compression resistant septum.

19. The catheter system of claim 18, wherein a septum chamber is intermediate the first compression resistant septum and the second compression resistant septum.

20. The catheter system of claim 10, further comprising a support element disposed between the grip and the needle hub.

* * * * *